United States Patent [19]
Katayama et al.

[11] Patent Number: 5,851,487
[45] Date of Patent: Dec. 22, 1998

[54] DATA CHECKING APPARATUS

[75] Inventors: Masayuki Katayama, Miki; Chisato Itoh, Kakogawa, both of Japan

[73] Assignee: Toa Medical Electronics Co., Ltd., Hyogo, Japan

[21] Appl. No.: 760,315

[22] Filed: Dec. 4, 1996

[30] Foreign Application Priority Data

Dec. 6, 1995 [JP] Japan .................................... 7-318199

[51] Int. Cl.⁶ .................................................. G01N 33/48
[52] U.S. Cl. ........................... 422/68.1; 422/55; 422/56; 422/82.05; 436/63; 356/73
[58] Field of Search .................... 436/8, 10, 14, 436/15, 63; 422/67, 68.1, 55, 56, 82.05; 356/73

[56] References Cited

U.S. PATENT DOCUMENTS 5,325,168  6/1994  Nakamoto et al. ........................ 356/73
5,325,169  6/1994  Nakamoto et al. ........................ 356/73

FOREIGN PATENT DOCUMENTS 0389992  10/1990  European Pat. Off. .
0599022  6/1994   European Pat. Off. .
2027262  1/1990   Japan .
5-322885 12/1993  Japan .

OTHER PUBLICATIONS

International Journal of Bio–Medical Computing, vol. 37 No. 1, Sep. 1, 1994, pp. 41–55, XP000474586, Somoza E: "Classification of Diagnostic Tests".

*Primary Examiner*—Maureen M. Wallenhorst

[57]    ABSTRACT

A data checking apparatus receives and checks observation data on a plurality of observation items including first and second observation items. The observation data is obtained by analyzing a single object with a plurality of analyzers including first and second analyzers. The apparatus includes an input device for inputting, beforehand, correlation data indicating correlation among the plurality of observation items, a memory for storing the input correlation data, a judgment device for cross-checking the observation data on the plurality of items to judge as to whether the received observation data conforms to the stored correlation data, and an output device for outputting results of the judgment.

8 Claims, 6 Drawing Sheets

| Rank | LL    |   | UL  |        |
|------|-------|---|-----|--------|
| 0    | 0     | – | 6   | [/uL]  |
| 1    | 6.1   | – | 28  | [/uL]  |
| 2    | 28.1  | – | 55  | [/uL]  |
| 3    | 55.1  | – | 110 | [/uL]  |
| 4    | 110.1 | – | 165 | [/uL]  |
| 5    | 165.1 | – | 275 | [/uL]  |
| 6    | 275.1 | – | 550 | [/uL]  |
| 7    | 550.1 | – | 0   | [/uL]  |
| 8    |       | – |     | [/uL]  |

DATA CHECKING APPARATUS

BACKGROUND OF THE INVENTION

1. Field of the Invention

The present invention relates to an apparatus for checking determinations in clinical analysis, particularly an apparatus for judging reliability of plural types of observations, for example, by urinary qualitative analysis and by urinary sediment analysis.

2. Description of Related Art

Conventionally, for urinalysis, two types of analysis are generally known, that is, qualitative analysis and sediment analysis. In the qualitative analysis, in general, a urinary sample to be analyzed is automatically determined to provide negative/positive observations such as (−), (±), (+), etc. on several observation items. For this purpose, a test sheet on[]which pieces of reactive papers for the observation items are affixed is dipped into the urinary sample for a required period of time, and the colors of the pieces after the dipping are compared with reference colors for determination (e.g., Japanese Unexamined Patent Publication No. Hei2(1990)-27262).

In the urinary sediment analysis, concrete components in a urinary sample to be analyzed are automatically classified and enumerated (e.g., Japanese Unexamined Patent Publication No. Hei5(1993)-322885).

In the qualitative analysis, errors in determination are sometimes found on some observation items because of inhibitory reactions. For example, the determination on occult blood (OB) is liable to present false negative in the presence of ascorbic acid, and false positive in the presence of hypochlorous acid.

Therefore there are demands for a judging apparatus which easily judges the reliability of the determination on each observation item in the qualitative analysis. Further, such an apparatus needs to be so flexible that it may be adjusted or calibrated easily and accurately in judging condition.

SUMMARY OF THE INVENTION

The present invention, in view of these circumstances, is to provide a data checking apparatus which is capable of obtaining observation data of a single object on a plurality of observation items and crosschecking the obtained observation data on the items to evaluate the reliability of the observation data.

Therefore, the present invention provides a data checking apparatus for receiving and checking observation data on a plurality of observation items including a first and a second observation item, the observation data being obtained by analyzing a single object with a plurality of analyzers including a first and a second analyzer, comprising: input means for beforehand inputting correlation data indicating correlation among the plural observation items; storage means for storing the input correlation data; judgment means for cross-cheking the observation data on the plural items to form a judgment as to whether the received observation data conforms to the stored correlation data; and output means for outputting the formed judgment.

The present invention will hereinafter be described in detail with reference to an embodiment.

DESCRIPTION OF THE PREFERRED EMBODIMENTS

The observation data on the plural observation items (the first observation item, the second observation item, etc.) can be obtained by analyzing the single object by the plural analyzers (the first analyzer, the second analyzer, etc.).

In the present invention, the test object is urine of a mammal, for example. A human being is included in mammals.

In the present invention, for example, the first analyzer may be a urinary sediment analyzer and the second analyzer may be a urinary qualitative analyzer.

It is preferable that, when the observation item determined by the urinary sediment analyzer is at least one selected from red blood cells, white blood cells, casts and bacteria and the observation item determined by the urinary qualitative analyzer is at least one selected from occult blood, protein, nitrites and white blood cells, the correlation data is set to indicate correlation between at least one combination selected from the combinations of red blood cells with occult blood, white blood cells with white blood cells, casts with protein, and bacteria with nitrites, considering close correlation between each of these combinations.

As the input means, a digitizing pad or a keyboard may be used. The storage means and the judgment means may comprise a microcomputer including CPU, ROM and RAM. As the output means, CRT, a liquid crystal display or a printer may be used.

The urinary sediment analyzer may be an apparatus for analyzing concrete components in urine using a flowcytometer and outputting obtained analysis results as the observation data.

The urinary qualitative analyzer may be an apparatus for dipping a test sheet into urine and outputting a degree of discoloration of the test sheet as the observation data.

When the stored correlation data is represented as an area on a coordinate system with the plural observation items as parameters, the judgment means can judge the degree of correlation of the received observation data based on whether the coordinates of the received observation data are within the area or how far the coordinates of the received observation data are from the area.

For any two of the plural observation items (e.g., the first and the second observation item), relevant correlation data may be represented on a two-dimensional coordinate plane.

The two-dimensional coordinate plane may be represented as a lattice obtained by grading each of the determination ranges for the first and the second observation item into a plurality of ranks, and the correlation data may be input as data corresponding to the lattice.

Embodiment

The present invention will, hereinafter be described in details by way of example with reference to accompanying figures, which are not intended to limit the scope of the invention.

Figure 1:
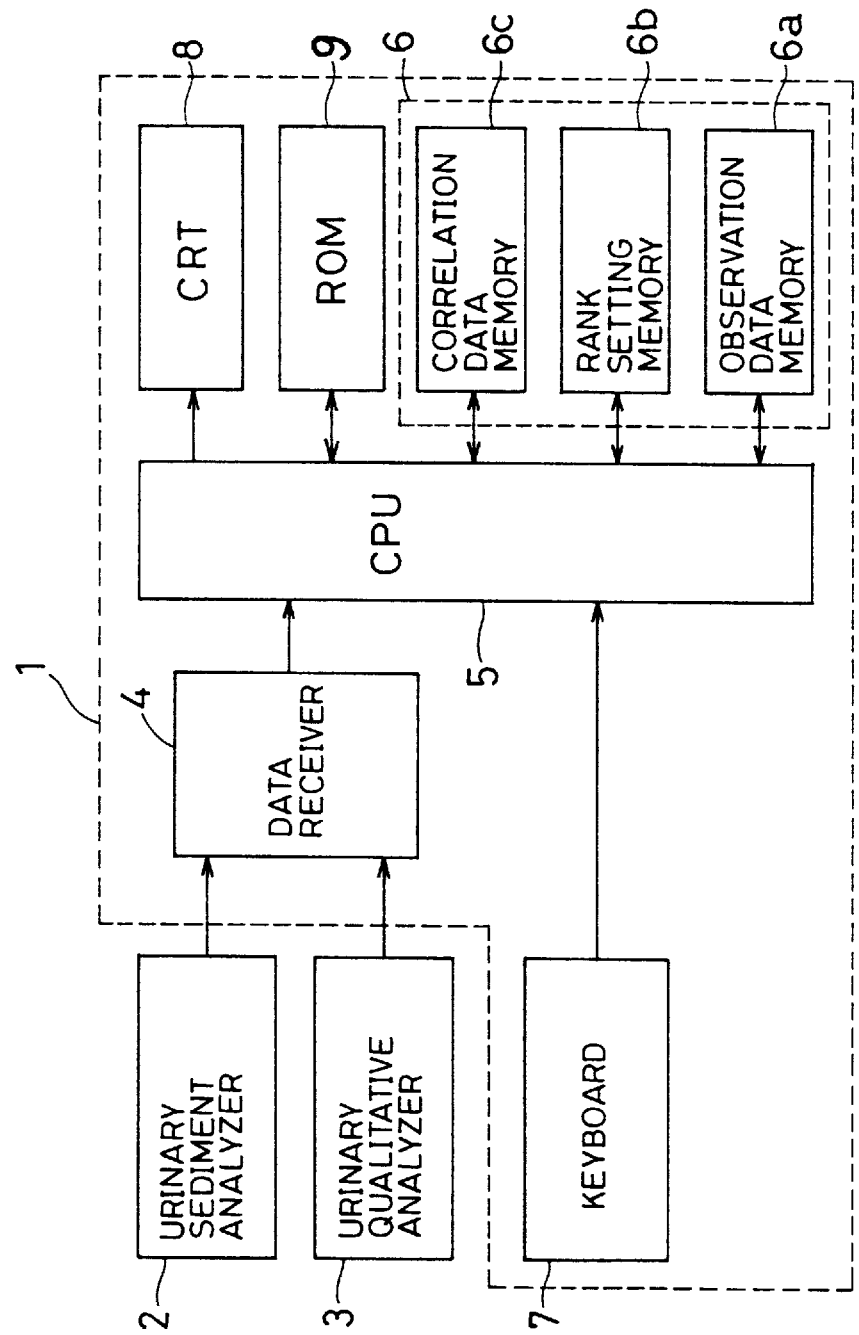
FIG. 1 is a block diagram illustrating the structure of an embodiment of the present invention.

FIG. 1 is a block diagram illustrating the structure of an embodiment of the data checking apparatus of the present invention. In FIG. 1, there are shown a data checking apparatus 1, a urinary sediment analyzer 2, a urinary qualitative analyzer 3 and a data receiver 4 for receiving observation data obtained by the urinary sediment analyzer 2 and the urinary qualitative analyzer 3.

In this embodiment, the urinary sediment analyzer 2 is a conventional analyzer which automatically determines concrete components in a urine sample by a flow cytometer and outputs, as the observation data, numeral values obtained by analysis, and the urinary qualitative analyzer 3 is a conventional analyzer which automatically classifies the degree of discoloration of a urinary test sheet dipped in the urine sample into one of nine grade ranks and outputs a symbol of (−), (±), (2+), (3+), . . . , or (7+) corresponding to the rank as the observation data.

The data receiver 4, for example, receives the observation data provided directly or via a communication circuit from the urinary sediment analyzer 2 and the urinary qualitative analyzer 3 and inputs the observation data to a CPU 5.

The observation data received by the data receiver 4 is stored in an observation data memory 6a of a RAM 6 via the CPU 5.

A reference numeral 7 denotes a keyboard for inputting correlation data, observation items and ranks for grading the determination range.

The ranks and the correlation data input by the keyboard 7 are stored in a rank-setting memory 6b and in a correlation data memory 6c of the RAM 6, respectively.

ROM 9 stores, beforehand, a control program for controlling the CPU 5, and a CRT displays the stored data, the observation data and judgment results.

The urinary sediment analyzer 2 performs determination on quantitative observation items by classification and enumeration. The quantitative observation items include red blood cells (RBC), white blood cells (WBC 1), epithelial cells (EC), casts (CAST) and bacteria (BACT).

The urinary qualitative analyzer 3 performs determination on qualitative observation items with a urinary test sheet. The qualitative observation items include occult blood (OB), protein (PRO), nitrites (NIT) and white blood cells (WBC 2).

Combinations of the quantitative and the qualitative observation items which show close correlation are RBC× OB, WBC 1×WBC 2, CAST×PRO and BACT×NIT, for example.

Here, taking the combination of RBC×OB for example, the correlation data indicating correlation between RBC and OB is input beforehand by the keyboard 7. Then, the data checking apparatus 1 receives the observation data on RBC and that on OB from the urinary sediment analyzer 2 and the urinary qualitative analyzer 3, respectively. Subsequently, the CPU 5 judges whether the received pair of data conforms to the relevant correlation data and displays the judgment on the CRT 8.

Operations in such a construction will now be described in detail.

Figure 5:
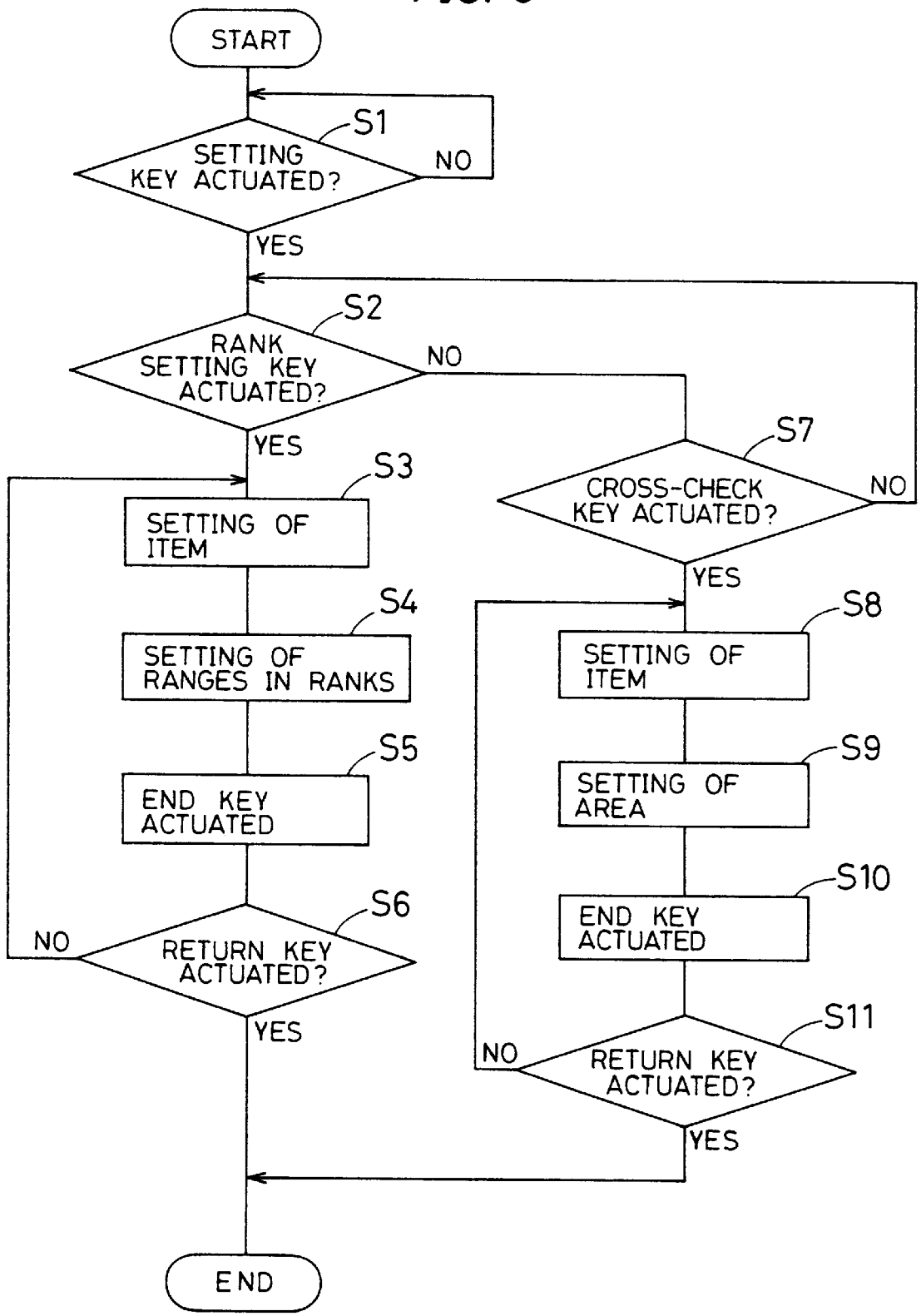
FIG. 5 is a flowchart illustrating operations in major portions of an embodiment.

First, procedure for setting the correlation data indicating correlation between the observation items will be explained with reference to a flowchart in FIG. 5.

Figures 2, 3:
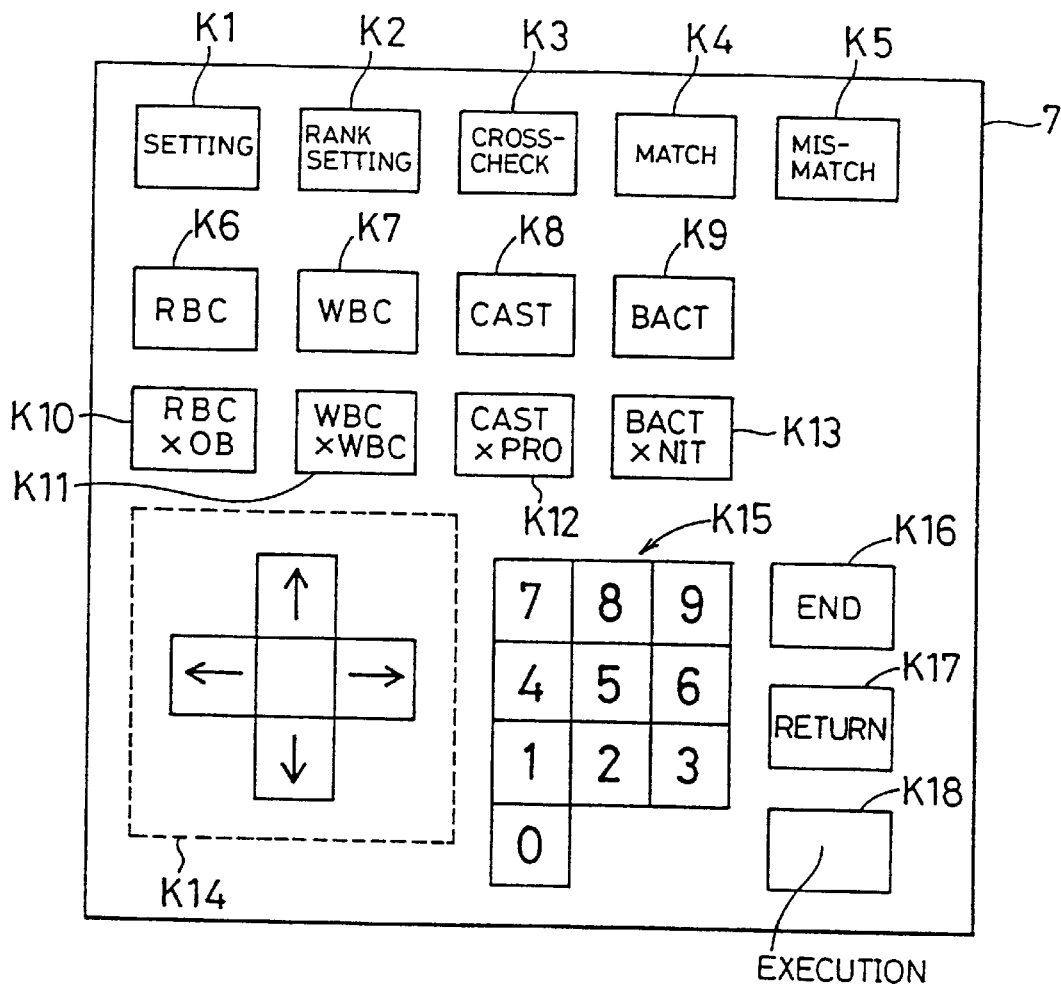
FIG. 2 is a detailed view of a major portion of FIG. 1.
FIG. 3 illustrates an exemplary display in an embodiment.

FIG. 2 illustrates key arrangement on the keyboard 7. By actuating a setting key K1 and a rank setting key K2 (steps S1 and S2), a rank setting mode is obtained and a display for rank setting shown in FIG. 3 is displayed on the CRT 8. Then, by actuating a key K6, RBC which is one of the quantitative observation items is selected (step S3).

Next, for each of ranks 0 to 8 on the display as shown in FIG. 3, a lower limit (LL) and an upper limit (UL) of RBC is set using cursor movement keys K14 and a numeric keypad K15 (step S4). By actuating an end key K16, the rank setting for RBC is completed (step S5).

In FIG. 3, the upper limit (UL) for the rank 7 is set to "0," which means "infinity" and no limits is set for the rank 8. Similarly, WBC, CAST, and BACT are sequentially selected using keys K7, K8, and K9, lower limits and upper limits are set for the ranks 0 to 8. Then by actuating a return key K17, the rank setting mode is terminated (step S6).

Figure 4:
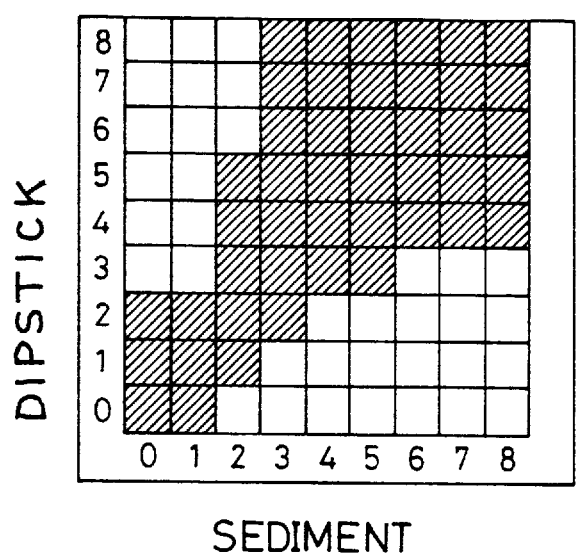
FIG. 4 illustrates another exemplary display in an embodiment.

Next, by actuating the setting key K1 and a cross-check key K3 (steps S1 and S7), an area setting mode is obtained, and a display for area setting shown in FIG. 4 is displayed on the CRT 8.

The area setting display has a two-dimensional coordinate plane with a quantitative observation item (SEDIMENT) and a qualitative observation item (DIPSTICK) plotted in abscissa and in ordinate, respectively. Each of the abscissa and the ordinate is divided into nine ranks, and thus the display is provided with squares corresponding to the ranks for setting an area.

The nine ranks 0 to 8 in the abscissa correspond to the "Rank" shown in FIG. 3 which are set in the aforesaid rank setting mode. Correspondence of the nine ranks in the ordinate to observations obtained by the urinary analyzer 3 is provided beforehand to the ROM 7 so that the ranks 0 to 8 correspond to the observations (−), (±), (+), (2+), . . . , (7+) respectively.

Next, a cross-check item, RBC×OB, is selected by actuating a key K10 (step S8). As indicated with oblique lines in FIG. 4, a matching area where RBC and OB correlate with each other is set by the square using the cursor movement keys K14 and a key 4 (step S4).

The fixed matching area can be canceled by the square using the cursor movement keys 14 and a key K5. Then the end key 16 is actuated to finish the area setting for RBC×OB (step S10).

Similarly, cross-check items, WBC×WBC, CAST×PRO, and BACT×NIT, are selected one by one using keys 11, K12, and K13, and the matching areas thereof are fixed. Then by actuating the return key K17, the area setting mode is terminated (step S11).

Figure 6:
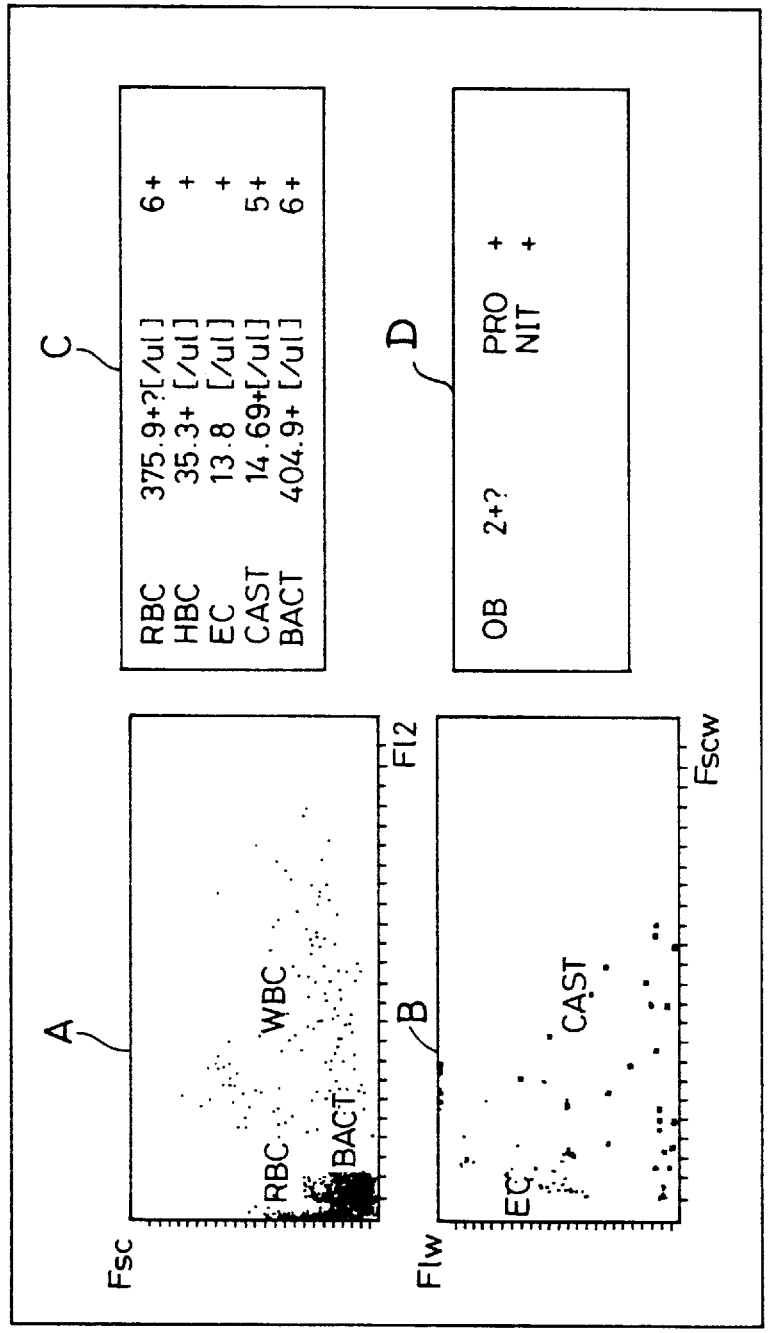
FIG. 6 illustrates exemplary displays in an embodiment.

Next, by actuating an execution key K18, an execution mode is obtained, in which the observation data obtained by the urinary sediment analyzer 2 and urinary qualitative analyzer 3 with respect to the same urine sample is read out from the observation data memory 6a and displayed on the CRT 8 as shown in FIG. 6.

FIGS. 6A and 6B show scattergrams based on observation data from the urinary sediment analyzer 2. FIG. 6C shows observation data from the urinary sediment analyzer 2 and the urinary qualitative analyzer 3 on observation items common to both the analyzers, i.e., RBC, WBC, EC, CAST, and BACT, and FIG. 6D shows observation data on the other items, i.e., OB, PRO and NIT from the urinary qualitative analyzer 3.

Each correlation between observation data on RBC and OB, WBC and WBC, CAST and PRO, and BACT and NIT is judged as to whether the coordinates of the observation data are within the relevant matching area fixed in the area setting mode. Any observation data outside the matching area is indicated with "?" as shown in FIG. 6C and 6D.

Referring to FIG. 6C and 6D, "375.9" on RBC and "2+" on OB have "?". This means that the observation data on this combination is crosschecked and observed not to be within the matching area shown in FIG. 4. In other words, the square defined by the rank 6 in the abscissa corresponding to "375.9" and the rank 3 in the ordinate corresponding to "2+" is not within the matching area.

Referring to FIG. 6C and 6D, the data with "?" is not reliable and the other data is reliable.

Thus the data observed by the urinary analyzer 2 and the urinary qualitative analyzer 3 can be cross-checked for the evaluation of the reliability thereof.

Figure 7:
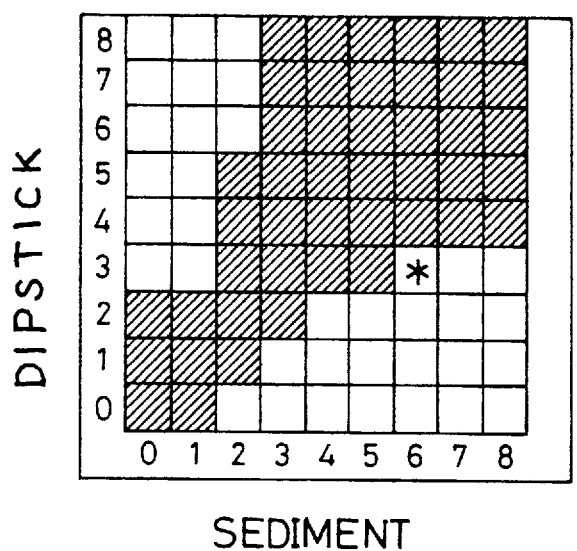
FIG. 7 illustrates an exemplary display in an embodiment.

Further, it is preferable that the observation data may be indicated with a sign such as * displayed in the square corresponding to the observation data on the area setting display presenting the matching area as shown in FIG. 7.

By such a display, it can be easily seen how far the observation data is apart from the matching area, and accordingly the degree of the reliability of the observation data can be checked also with the eyes of a user.

Though, in this embodiment, the ranges of the observation data corresponding to the ranks 0 to 8 in the ordinate in FIG. 4 are set beforehand in the ROM 7, alternatively the ranges may be optionally set by a user in the rank setting memory 6b just as the ranks in the abscissa.

The data check apparatus I may be incorporated in either the urinary sediment analyzer 2 or the urinary qualitative analyzer 3. Additionally, the occult blood and the white blood cell in the qualitative observation items may be sometimes represented as (OB/Hb) and (L.EST.) respectively.

According to the present invention, observation data on the same test object obtained by different analyzers are cross-checked, so that the reliability of the observation data can be easily evaluated.

What is claimed is:

1. An apparatus for checking observation data obtained by analyzing a specimen with a plurality of analyzers, comprising:

a first analyzer for analyzing a specimen by a first method to obtain first observation data on one or more first observation items;

a second analyzer for analyzing the specimen by a second method to obtain second observation data on one or more second observation items;

input means for inputting, prior to an analysis operation by the first and second analyzers, correlation data indicating a desired correlation between the first and second observation items to evaluate reliability of the first and second observation data;

storage means for storing the input correlation data, the stored correlation data being represented as an area on a two dimensional coordinate system defined by parameters representing the first and the second observation items;

judgement means for making a judgment as to whether the first and second observation data conform to the stored correlation data based on whether coordinates representative of the first and second observation data are within the area;

output means for outputting results of the judgement; and display means for displaying the coordinate system representing the stored correlation data and a sign representative of the coordinates of the first and second observation data on the coordinate system.

2. The apparatus of claim 1, wherein the specimen analyzed is urine of a mammal, the mammal including a human being.

3. The apparatus of claim 2, wherein the first analyzer is a urinary sediment analyzer and the second analyzer is a urinary qualitative analyzer.

4. The apparatus of claim 3, wherein the first observation items are selected from the group consisting of red blood cells, white blood cells, casts, and bacteria, the second observation items are selected from the group consisting of occult blood, protein, nitrites, and white blood cells, and the correlation data indicates correlation of at least one combination of red blood cells with occult blood, white blood cells with white blood cells, casts with protein, and bacteria with nitrites.

5. The apparatus of claim 3, wherein the urinary sediment analyzer includes an apparatus for analyzing particle components in urine by a flow cytometer to output the first observation data.

6. The apparatus of claim 3, wherein the urinary qualitative analyzer includes an apparatus for dipping a test sheet into urine to output a degree of discoloration of the test sheet as the second observation data.

7. The apparatus of claim 1, wherein the two-dimensional coordinate system is defined by a lattice for grading each of the parameters representative of the first and second observation items into a plurality of ranks and the correlation data is input as data corresponding to the lattice.

8. An apparatus for checking observation data obtained by analyzing a specimen with a plurality of analyzing methods, comprising:

receiving means for receiving first observation data on a first observation item obtained by analyzing a specimen with a first method and second observation data on a second observation item obtained by analyzing the specimen with a second method;

input means for inputting correlation data indicating a desired correlation between the first and second observation items to evaluate reliability of the first and second observation data;

storage means for storing the input correlation data, the stored correlation data being represented as an area on a two-dimensional coordinate system defined by parameters representing the first and second observation items;

judgment means for making a judgment as to whether the received first and second observation data conform to the input correlation data based on whether coordinates representative of the first and second observation data are within the area;

output means for outputting results of the judgment; and display means for displaying the coordinate system representing the stored correlation data and a sign representative of the coordinates of the first and second observation data on the coordinate system.

* * * * *